United States Patent
Young et al.

(10) Patent No.: US 9,553,034 B1
(45) Date of Patent: Jan. 24, 2017

(54) COMBINED SEMICONDUCTOR METROLOGY SYSTEM

(75) Inventors: Scott A. Young, Soquel, CA (US); Guoheng Zhao, Milpitas, CA (US); NanChang Zhu, Shanghai (CN); Neeraj Khanna, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 840 days.

(21) Appl. No.: 13/533,360

(22) Filed: Jun. 26, 2012

Related U.S. Application Data

(60) Provisional application No. 61/623,997, filed on Apr. 13, 2012, provisional application No. 61/616,072, filed on Mar. 27, 2012.

(51) Int. Cl.
*H01L 21/66* (2006.01)
*G01N 21/95* (2006.01)

(52) U.S. Cl.
CPC ........... *H01L 22/24* (2013.01); *G01N 21/9503* (2013.01); *H01L 22/12* (2013.01)

(58) Field of Classification Search
CPC ................ G01N 21/9501; G01N 21/95607; G02B 21/0064; G02B 21/0016; G02B 6/0051
See application file for complete search history.

(56) References Cited

U.S. PATENT DOCUMENTS

| | | | |
|---|---|---|---|
| 6,003,992 A * | 12/1999 | Bergeron Dunn et al. | 351/221 |
| 6,580,502 B1 * | 6/2003 | Kuwabara | G01N 21/9501 250/559.41 |
| 7,740,371 B1 * | 6/2010 | Lebens et al. | 362/205 |
| 8,023,110 B1 * | 9/2011 | Ngai et al. | 356/237.1 |
| 2002/0140930 A1 * | 10/2002 | Lin et al. | 356/237.2 |
| 2010/0026997 A1 * | 2/2010 | Hayashi et al. | 356/237.5 |
| 2010/0188499 A1 * | 7/2010 | Amanullah et al. | 348/87 |
| 2012/0176486 A1 * | 7/2012 | Maeda et al. | 348/68 |
| 2012/0262566 A1 | 10/2012 | Grzegorczyk et al. | |
| 2012/0293669 A1 * | 11/2012 | Mann et al. | 348/207.11 |
| 2013/0242303 A1 * | 9/2013 | Liu | 356/369 |

OTHER PUBLICATIONS

Park, Jong-II, et al. "Multispectral imaging using multiplexed illumination."Computer Vision, 2007. ICCV 2007. IEEE 11th International Conference on. IEEE, 2007.*

* cited by examiner

*Primary Examiner* — Sath V Perungavoor
*Assistant Examiner* — Clifford Hilaire
(74) *Attorney, Agent, or Firm* — Suiter Swantz pc llo

(57) ABSTRACT

A semiconductor wafer inspection system includes a camera and two or more illuminators. The illuminators illuminate a line of the semiconductor wafer in sequence and the camera captures an interleaved image of illuminated lines such that the individual images can be recovered from the interleaved image. The semiconductor wafer can be moved by a conveyor so that adjacent lines can be sequentially illuminated by the illuminators. The camera may include two or more line sensors.

28 Claims, 14 Drawing Sheets

COMBINED SEMICONDUCTOR METROLOGY SYSTEM

PRIORITY

The present application claims the benefit under 35 U.S.C. §119(e) of U.S. Provisional Application Ser. No. 61/623,997, filed Apr. 13, 2012, and U.S. Provisional Application Ser. Nos. 61/616,072, filed Mar. 27, 2012, which are incorporated herein by reference.

FIELD OF THE INVENTION

The present invention is directed generally toward semiconductor metrology and inspection, and more particularly toward illumination and imaging.

BACKGROUND OF THE INVENTION

Photoluminescence imaging and micro-crack detection are important inspection procedures in semiconductor wafer processing. Transmitted or reflected images of a semiconductor wafer are taken with line scan image cameras and analyzed for, among other things, micro-cracks and photoluminescence features.

One of the challenges facing the solar industry is to lower the cost of manufacturing solar cells. Current systems utilize a single illuminator and camera for each image to be taken during the inspection process. Cameras useful for current semiconductor inspection processes are expensive; cost of inspection becomes a significant factor of manufacturing when multiple cameras are needed to collect multiple images to evaluate various proprieties of samples. In addition, a failure of any one camera in an inspection system may compromise the entire process; therefore reliability may suffer with each additional camera in the system.

Consequently, it would be advantageous if an apparatus existed that is suitable for imaging semiconductor wafers illuminated by multiple wavelengths and at multiple angles with a single camera, and minimize the number of cameras needed to acquire multiple properties of the samples.

SUMMARY OF THE INVENTION

Accordingly, the present invention is directed to a novel method and apparatus for imaging semiconductor wafers in multiple wavelengths and at multiple angles with a single camera, which also reduces the number of cameras required for simultaneous imaging of multiple wavelengths.

In one embodiment, two or more illuminators operating at different wavelengths illuminate a semiconductor wafer at discreet intervals, and images of the illuminated semiconductor wafer are captured by a camera. The images may be optical images (transmitted, reflected, or scattered) at the same wavelength of the illuminator or photoluminescence images at a different wavelength from the illumination wavelength.

In another embodiment, two or more illuminators illuminate a semiconductor wafer at different angles and at discreet intervals, and images of the illuminated semiconductor wafer are captured by a camera. The images may be transmission images or reflection images.

In another embodiment, a method of inspecting a semiconductor wafer includes capturing three or more at least two separate images of the semiconductor wafer, illuminated by at least two separate illuminators, with a single camera, then analyzing the separate images for micro-cracks.

In another embodiment, a method of inspecting a semiconductor wafer includes capturing images at multiple wavelengths and multiple angles with a single camera, then analyzing the three or more images for micro-cracks and photoluminescence features.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles.

BRIEF DESCRIPTION OF THE DRAWINGS

The numerous objects and advantages of the present invention may be better understood by those skilled in the art by reference to the accompanying figures in which.

DETAILED DESCRIPTION OF THE INVENTION

This application is related to U.S. patent application Ser. No. 13/376,480 filed Dec. 16, 2011, which is hereby incorporated by reference. Reference will now be made in detail to the subject matter disclosed, which is illustrated in the accompanying drawings. The scope of the invention is limited only by the claims; numerous alternatives, modifications and equivalents are encompassed. For the purpose of clarity, technical material that is known in the technical fields related to the embodiments has not been described in detail to avoid unnecessarily obscuring the description.

Figure 1:
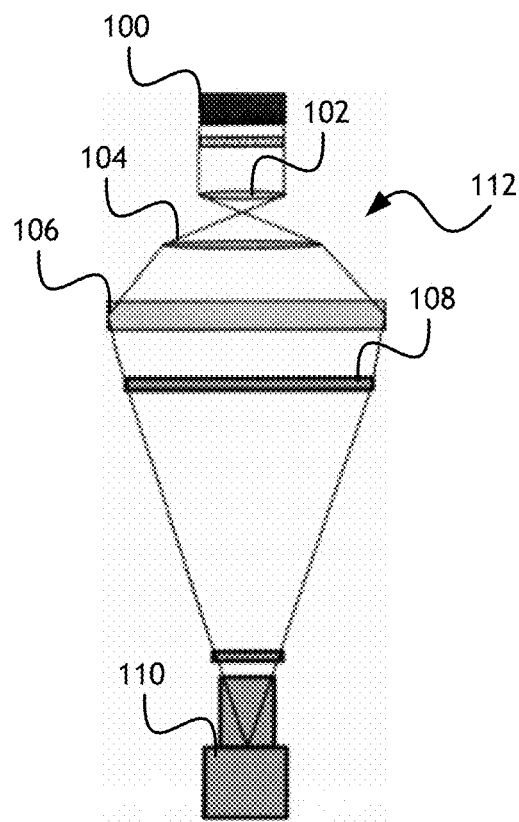
FIG. 1 shows a block diagram of a system for imaging a semiconductor wafer.

Referring to FIG. 1, a block diagram of a system for imaging a semiconductor wafer is shown. The system may include an illuminator 100 such as a laser bar comprising quasi-continuous wave laser diodes. The illuminator 100 may produce light in a specific wavelength or range of wavelengths to illuminate micro-cracks or other defects in a semiconductor wafer 108; such wavelengths may include, but are not limited to, ultraviolet, visible, near infrared and infrared. The system may also include a lens assembly 112 to focus light from the illuminator 100 onto the semiconductor wafer 108 or some portion of the semiconductor wafer 108.

The lens assembly 112 may include a first complimentary lens 102 and a second complimentary lens 104 to spread and focus light from the illuminator 100. The lens assembly 112 may also include a cylinder field lens 106 to focus light from the first complimentary lens 102 and the second complimentary lens 104 onto a portion of the semiconductor wafer 108; for example, the cylinder field lens 106 may focus the light into a line or narrow band on the semiconductor wafer.

The system may also include an imaging device 110, such as a line scan image camera, appropriate for imaging a semiconductor wafer in a micro-crack inspection process. In some embodiments, the imaging device 110 may include filters. The imaging device 110 may transfer any captured images to a computer for processing and analysis to identify any defects such as micro-cracks.

Semiconductor wafer inspection may involve images produced by transmitted light or reflected light. Those skilled in the art may appreciate that inspection using either transmitted or reflected light may require illuminators 100 operating in certain specific wavelength ranges and imaging devices 110 capable of capturing images in certain specific wavelength ranges. In either case, the range of wavelengths may dictate the specific characteristics of the elements of the lens assembly 112.

While FIG. 1 illustrates an illuminator 100 illuminating a semiconductor wafer 108 with light substantially normal to the surface of the semiconductor wafer 108; the illuminator 100 may also illuminate the semiconductor wafer 108 at an angle. Illumination at an angle may improve illumination of defects that may not be visible otherwise.

Figure 2:
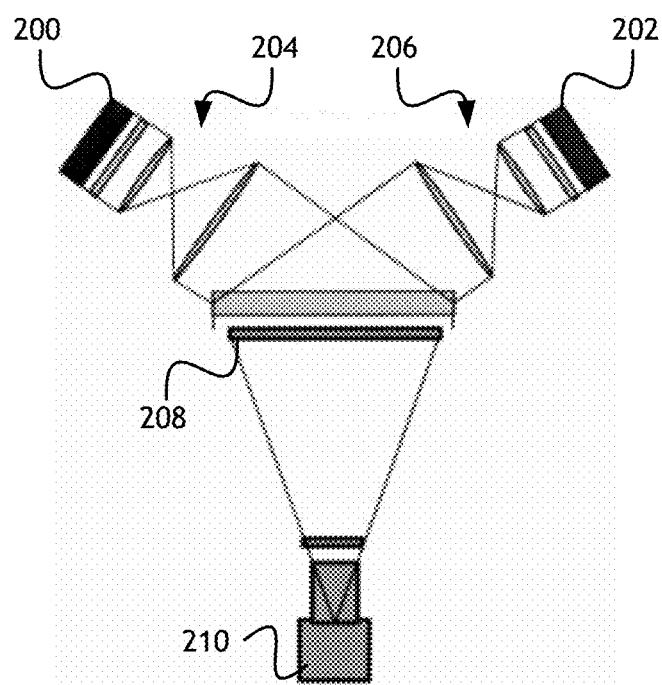
FIG. 2 shows a block diagram of a system with two angled illuminators for imaging a semiconductor wafer.
Figure 3:
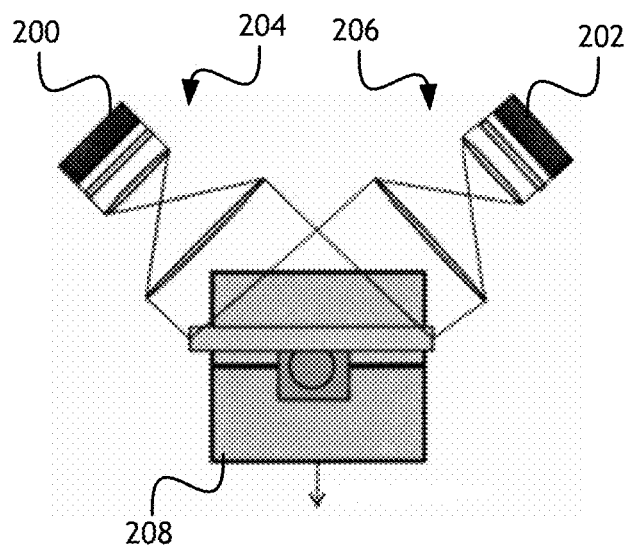
FIG. 3 shows a top view block diagram of the system in FIG. 2.

Referring to FIG. 2 and FIG. 3, a block diagram of a system with two angled illuminators for imaging a semiconductor wafer is shown. The system may include a first illuminator 200 and lens assembly 204 for projecting light onto a semiconductor wafer 208. The first illuminator 200 and lens assembly 204 may be positioned to project light at some angle to the surface of the semiconductor wafer 208. Light projected at an angle may enhance defect detection in some cases.

The system may also include a second illuminator 202 and lens assembly 206 for projecting light onto a semiconductor wafer 208. The second illuminator 202 and lens assembly 206 may be positioned to project light at some angle to the surface of the semiconductor wafer 208 different from the angle of the first illuminator 200 and lens assembly 204. The first illuminator 200 and second illuminator 202 may be positioned above or below the semiconductor wafer 208, at any azimuth to the semiconductor wafer 208, or positioned for bright field transmission or dark field transmission.

The system may also include an imaging device 210 to capture images of the semiconductor wafer 208 produced by transmitted light from the first illuminator 200 or second illuminator 202.

Each of the first illuminator 200 and the second illuminator 202 may produce pulses of light at a certain frequency, offset from each other such that only one illuminator 200, 202 illuminates the semiconductor wafer 208 at a time. Furthermore, the imaging device 210 may include a shutter synchronized to the frequencies of the illuminators 200, 202 to capture separate images produced by each illuminator 200, 202. In one embodiment, each illuminator 200, 202 may illuminate a line in the same location so that the imaging device 210 (a line camera) can capture a line image derived from each illuminator 200, 202 sequentially. Each image may be over-sampled or under-sampled depending on the number of lines captured within the optical point spread function. The imaging device 210 may thereby produce an interleaved line image. The interleaved line image may then be separated into separate two dimensional semiconductor wafer images by a processor for algorithmic processing and analysis.

Figure 4:
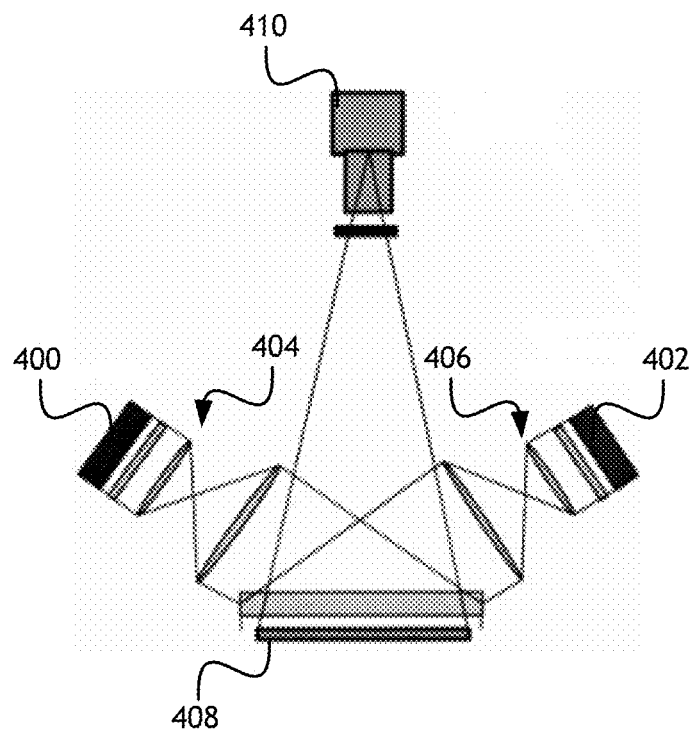
FIG. 4 shows a block diagram of a system with two angled illuminators for imaging a semiconductor wafer through reflection.

Referring to FIG. 4, a block diagram of a system with two angled illuminators for imaging a semiconductor wafer through reflection is shown. The system may include a first illuminator 400 and lens assembly 404 for projecting light onto a semiconductor wafer 408. The first illuminator 400 and lens assembly 404 may be positioned to project light at some angle to the surface of the semiconductor wafer 408. Light projected at an angle may enhance defect detection in some cases.

The system may also include a second illuminator 402 and lens assembly 406 for projecting light onto a semiconductor wafer 408. The second illuminator 402 and lens assembly 406 may be positioned to project light at some angle to the surface of the semiconductor wafer 408 different from the angle of the first illuminator 400 and lens assembly 404. The first illuminator 400 and second illuminator 402 may be positioned above or below the semiconductor wafer 408, at any azimuth to the semiconductor wafer 408, or positioned for bright field reflection or dark field reflection.

The system may also include an imaging device 410 to capture images of the semiconductor wafer 408 produced by reflected light from the first illuminator 400 or second illuminator 402.

Each of the first illuminator 400 and the second illuminator 402 may produce pulses of light at a certain frequency, offset from each other such that only one illuminator 400, 402 illuminates the semiconductor wafer 408 at a time. Furthermore, the imaging device 410 may include a shutter synchronized to the frequencies of the illuminators 400, 402 to capture separate images produced by each illuminator 400, 402. In one embodiment, each illuminator 400, 402 may illuminate a line in the same location so that the imaging device 410 (a line camera) can capture a line image derived from each illuminator 400, 402 sequentially. Each image may be over-sampled or under-sampled depending on the number of lines captured within the optical point spread function. The imaging device 410 may thereby produce an interleaved line image. The interleaved line image may then be separated into separate two dimensional semiconductor wafer images by a processor for algorithmic processing and analysis.

Figure 5:
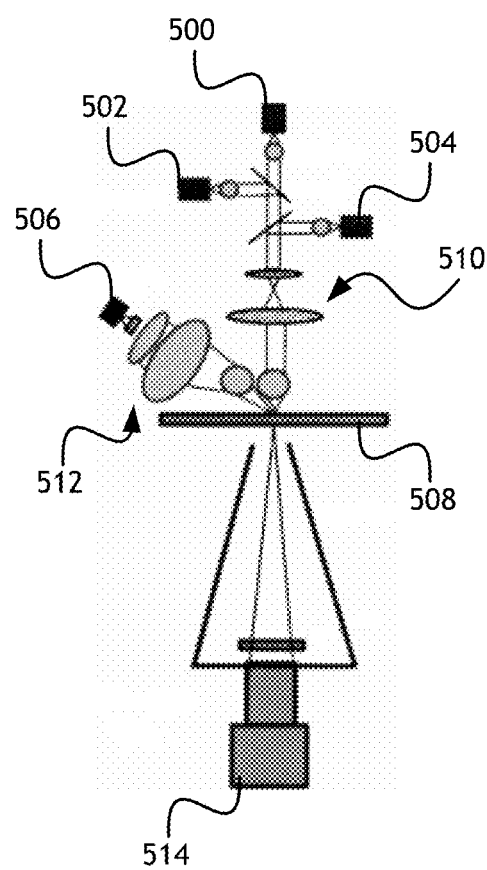
FIG. 5 shows a block diagram of a system with three illuminators for in-line illumination and illuminators for angled illumination for imaging a semiconductor wafer.
Figure 6:
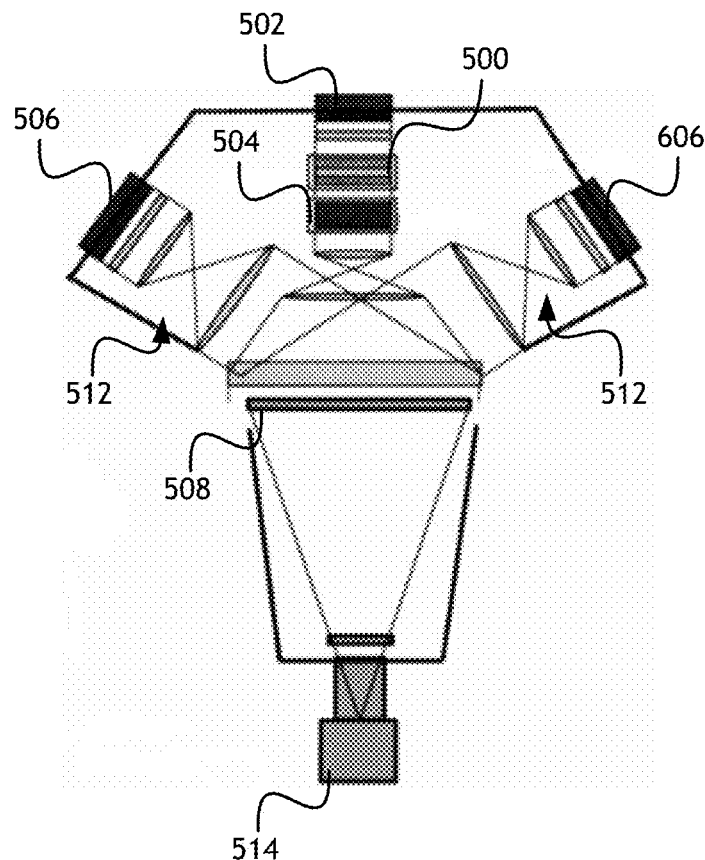
FIG. 6 shows a side view block diagram of the system in FIG. 5.
Figure 7:
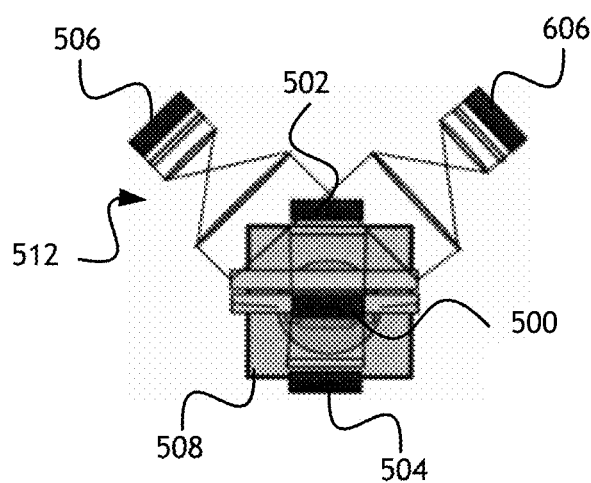
FIG. 7 shows a top view block diagram of the system in FIG. 5.

Referring to FIG. 5, FIG. 6 and FIG. 7, a block diagram of a system with three illuminators for in-line illumination and illuminators for angled illumination for imaging a semiconductor wafer is shown. The system may include a first in-line illuminator 500 for projecting light onto a semiconductor wafer 508. The first in-line illuminator 500 may project light at some specific wavelength onto the surface of the semiconductor wafer 508. The system may also include a second in-line illuminator 502 for projecting light onto a semiconductor wafer 508. The second in-line illuminator 502 may project light at some specific wavelength onto the surface of the semiconductor wafer 508 different from the wavelength of the first in-line illuminator 500. The first in-line illuminator 500 or second in-line illuminator 502 may project light through splitters or other optical components 510 such that each in-line illuminator 500, 502 may illuminate the same relative location of the semiconductor wafer 508, at the same relative angle. The wavelengths of the first in-line illuminator 500 and the second in-line illuminator 502 may be, but are not limited to, red, near infrared and infrared.

The system may also include an imaging device 514 to capture images of the semiconductor wafer 508 produced by transmitted light from the first in-line illuminator 500 or second in-line illuminator 502.

Each of the first in-line illuminator 500 and the second in-line illuminator 502 may produce pulses of light at a certain frequency, offset from each other such that only one in-line illuminator 500, 502 illuminates the semiconductor wafer 508 at a time. Furthermore, the imaging device 514 may include a shutter synchronized to the frequencies of the in-line illuminators 500, 502 to capture separate images produced by each in-line illuminator 500, 502. In one embodiment, each in-line illuminator 500, 502 may illuminate a line in the same location so that the imaging device 514 (a line camera) can capture a line image derived from each in-line illuminator 500, 502 sequentially. Each image may be over or under sampled depending on the number of lines captured within the optical point spread function. The imaging device 514 may thereby produce an interleaved line image. The interleaved line image may then be separated into separate two dimensional semiconductor wafer images by a processor for algorithmic processing and analysis.

The system may further include a third in-line illuminator 504. The third in-line illuminator 504 may project light at some specific wavelength onto the surface of the semiconductor wafer 508 different from the wavelength of either the first in-line illuminator 500 or the second in-line illuminator 502. The third in-line illuminator 504 may project light through splitters or other optical components such that each in-line illuminator 500, 502, 504 may illuminate the same relative location of the semiconductor wafer 508, at the same relative angle.

The system may also include a first angled illuminator 506 and lens assembly 512 for projecting light onto a semiconductor wafer 508. The first angled illuminator 506 and lens assembly 512 may be positioned to project light at some angle to the surface of the semiconductor wafer 508. Light projected at an angle may enhance defect detection in some cases.

The system may also include a second angled illuminator 606 and lens assembly 512 for projecting light onto a semiconductor wafer 508. The second angled illuminator 606 and lens assembly 512 may be positioned to project light at some angle to the surface of the semiconductor wafer 508 different from the angle of the first angled illuminator 506 and lens assembly 512. The first angled illuminator 506 and second angled illuminator 606 may be positioned above or below the semiconductor wafer 508, at any azimuth to the semiconductor wafer 508, or positioned for bright field reflection or dark field reflection.

In this embodiment, each in-line illuminator 500, 502, 504, and each angled illuminator 506, 606 may illuminate a line in the same location so that the imaging device 514 (a line camera) can capture a line image derived from each in-line illuminator 500, 502, 504 and angled illuminator 506, 606 sequentially. A processor may then process the images.

Figure 8:
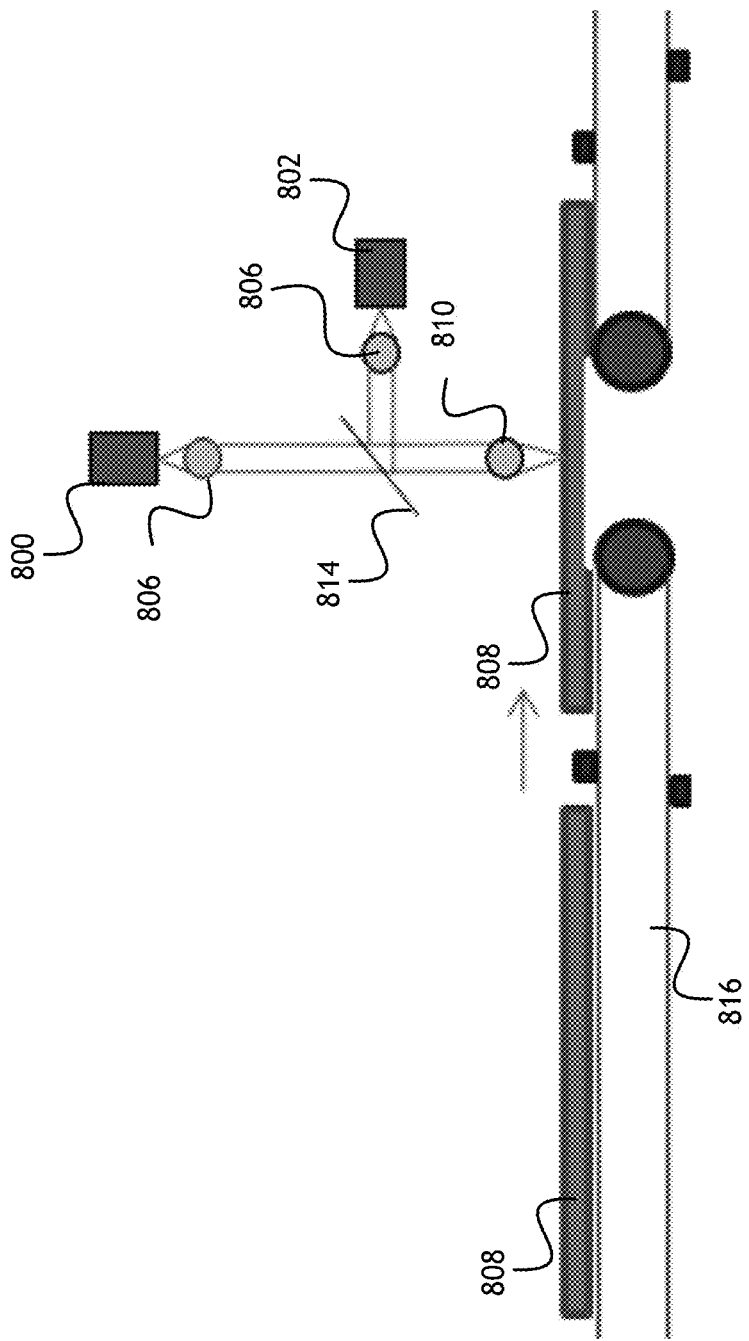
FIG. 8 shows a block diagram of a system with two inline illuminators.

Referring to FIG. 8, a block diagram of a system with two inline illuminators is shown. Illumination with laser diodes may require optical elements or optical fiber to spread and focus the laser light. Optical elements may reduce the efficiency of a system. Laser diodes may be stacked but stacking may limit cooling efficiency.

Embodiments of the present invention may include one or more laser bars 800, 802 to illuminate a portion of a semiconductor wafer 808. Laser bars 800, 802 may require only a collimating cylinder 806 to collimate the laser light and a cylinder field lens 810 to focus the collimated laser light onto a desired portion (line) of the semiconductor wafer 808. A line camera may then capture an image of the illuminated portion. Cooling may be handled with a water cooling manifold.

Collimated light from a first laser bar 800 and from a second laser bar 802 may be directed at a cylinder field lens 810 from the same direction through a beam splitter or other appropriate optical component. Furthermore, the semiconductor wafer 808 may be periodically moved relative to a stationary cylinder field lens 810 by a conveyor 816.

Figure 9:
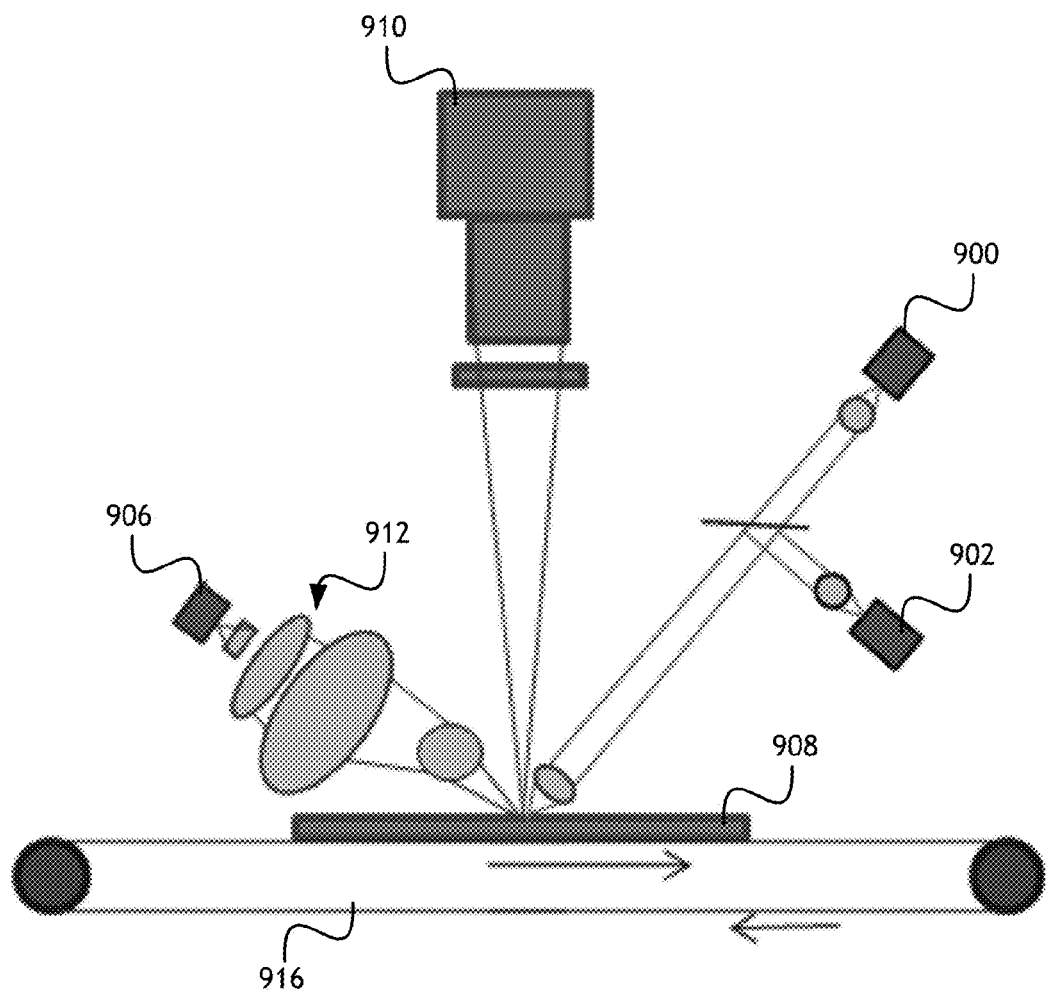
FIG. 9 shows a block diagram of a system for imaging a semiconductor wafer through reflection.

Referring to FIG. 9, a block diagram of a system for imaging a semiconductor wafer through reflection is shown. Embodiments of the present invention may include one or more laser bars 900, 902 to illuminate a portion of a semiconductor wafer 908 at different wavelengths, and one or more angled laser bars 906 to illuminate a portion of a semiconductor wafer 908 at different angles. Light from the one or more angled laser bars 906 may be focused through a system of optical elements 912 to illuminate the semiconductor wafer 908 at a desired angle. Light form the one or more laser bars 900, 902 or one or more angled laser bars 906 may reflect off of the semiconductor wafer 908 to a line camera 910. The line camera 910 may capture an interleaved image comprising lines of the semiconductor wafer 908 illuminated by each of the laser bars 900, 902 and angled laser bars 906 such that at least two complete images of at least a portion of the semiconductor wafer 908 can be recovered from the interleaved image; each of the at least two complete images comprising an image of a portion of the semiconductor wafer 908 illuminated by separate laser bars 900, 902 or angled laser bars 906. The line camera 910 may capture images of adjacent lines of the semiconductor wafer 908 as the semiconductor wafer 908 is moved by a conveyor 916.

Figure 10:
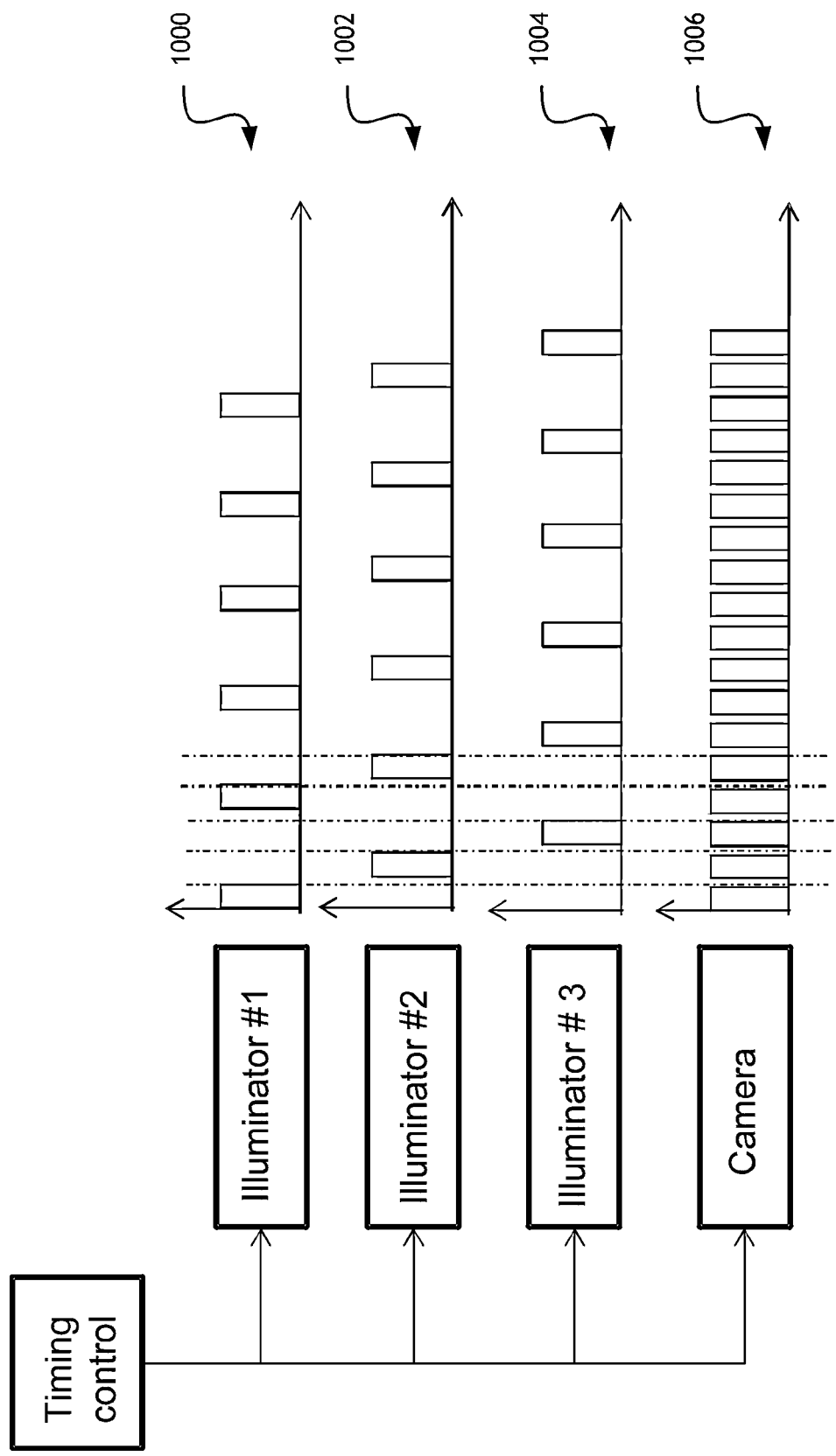
FIG. 10 shows a chart of timing intervals for a controller and a plurality of illuminators to capture differently illuminated images of portions of a semiconductor wafer with a single line camera.
Figure 11:
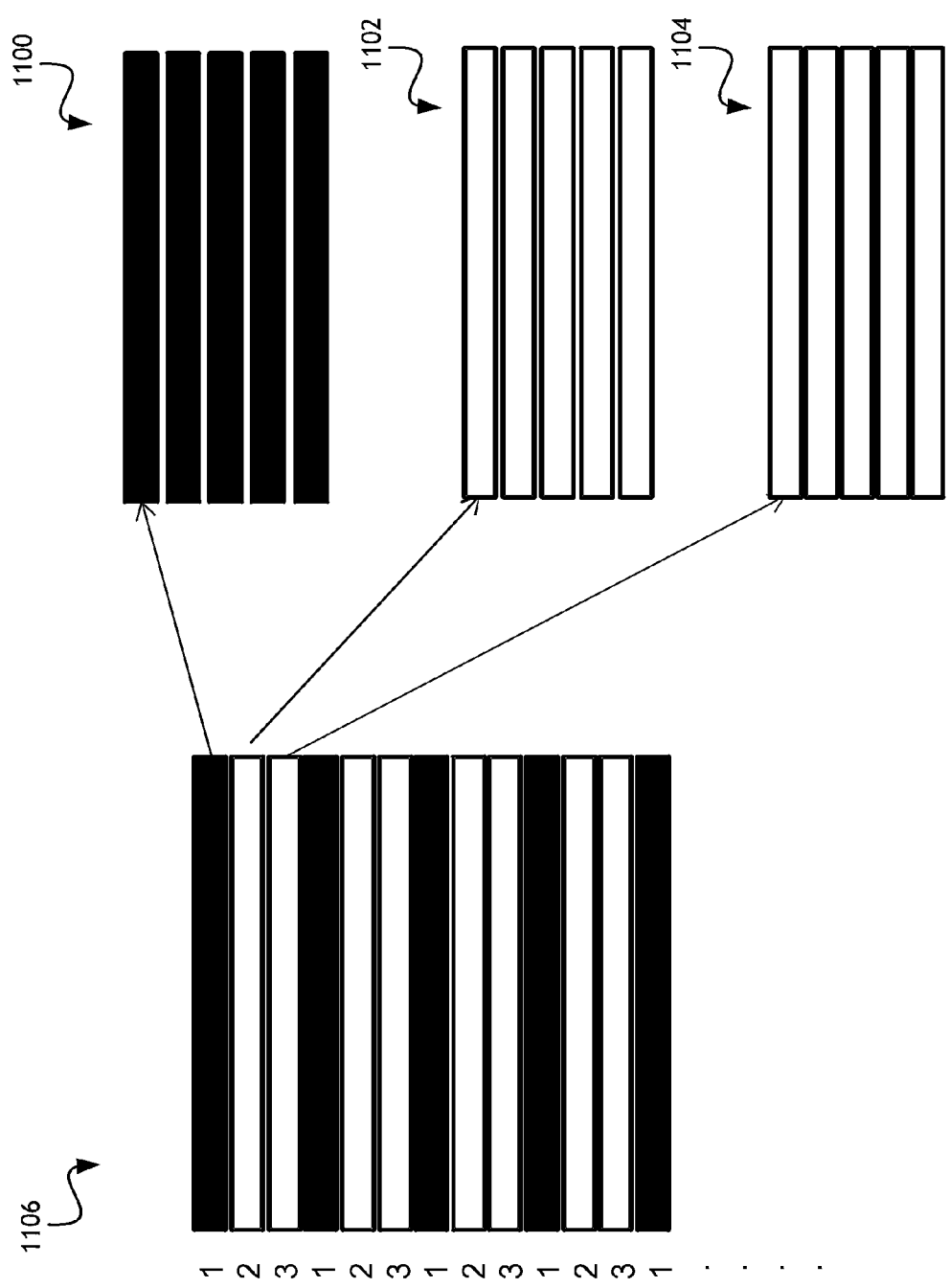
FIG. 11 shows a chart of reconstructed images captured by a line camera.

Referring to FIG. 10 and FIG. 11, a chart of timing intervals for a controller and a plurality of illuminators to capture differently illuminated images of portions of a semiconductor wafer with a single line camera and a chart of reconstructed images is shown. Embodiments of the present invention may include a line camera to capture images of a semiconductor wafer illuminated by two or more illuminators. The two or more illuminators may illuminate the semiconductor wafer periodically with the period of illumination for each illuminator offset from the period of illumination for each other illuminator such that only one illuminator is active at any one time. Furthermore, the line camera may operate at a capture frequency to capture one line per illuminator per period.

For example, a system may include three illuminators and a camera, all connected to a processor configured to timing control. A first illuminator may illuminate a portion of a semiconductor wafer 1000 for some duration of time; the line camera may capture 1006 one line illuminated by the first illuminator during that duration. The first illuminator would then stop illuminating and a second illuminator may illuminate the portion of the semiconductor wafer 1002 for some duration of time; the line camera may capture 1006 one line illuminated by the second illuminator during that duration. The second illuminator would then stop illuminating and a third illuminator may illuminate the portion of the semiconductor wafer 1004 for some duration of time; the line camera may capture 1006 one line illuminated by the third illuminator during that duration. The semiconductor wafer may then move such that the illuminators and line camera may address an adjacent line on the semiconductor wafer and the process may repeat. In this manner, the line camera may produce an interleaved image 1106 comprising three different reference images 1100, 1102, 1104. A processor may separate each of the reference images 1100, 1102, 1104 from the interleaved image 1106 for later analysis.

Reference images 1100, 1102, 1104 may comprise images of the same portion of a semiconductor wafer illuminated at different angles or by different wavelengths of light. For example, a first reference image 1100 may comprise an image of a portion of a semiconductor wafer illuminated by a first wavelength range, a second reference image 1102 may comprise an image of a portion of a semiconductor wafer illuminated by a second wavelength range and a third reference image 1104 may comprise an image of a portion of a semiconductor wafer illuminated by a third wavelength range.

Figure 12:
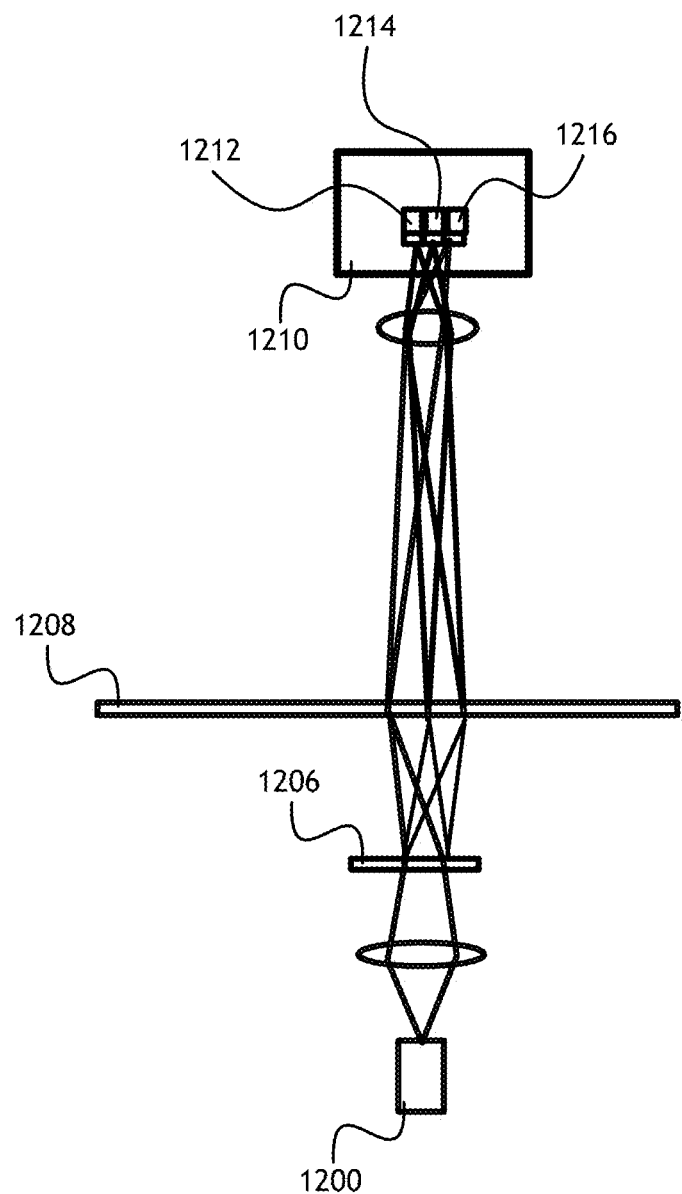
FIG. 12 shows a block diagram of a camera having more than one line sensor capturing images of a semiconductor wafer illuminated by different wavelength of laser light.

Referring to FIG. 12, a block diagram of a camera having more than one line sensor capturing images of a semiconductor wafer illuminated by different wavelengths of laser light is shown. Such embodiment may include an illuminator 1200. The illuminator 1200 may illuminate a semiconductor wafer 1208 so as to transmit light through the semiconductor wafer 1208 to a line camera 1210. Light from the illuminator 1200 may pass through a beam splitter 1206 before reaching the semiconductor wafer 1208 to produce two or more separate beams. Each of the two or more separate beams may be focused on a separate line sensor 1210, 1212, 1214 within the line camera 1210. Each line sensor 1210, 1212, 1214 may include a different spectral filter so that each line sensor 1210, 1212, 1214 records light in a different wavelength band.

Figure 13:
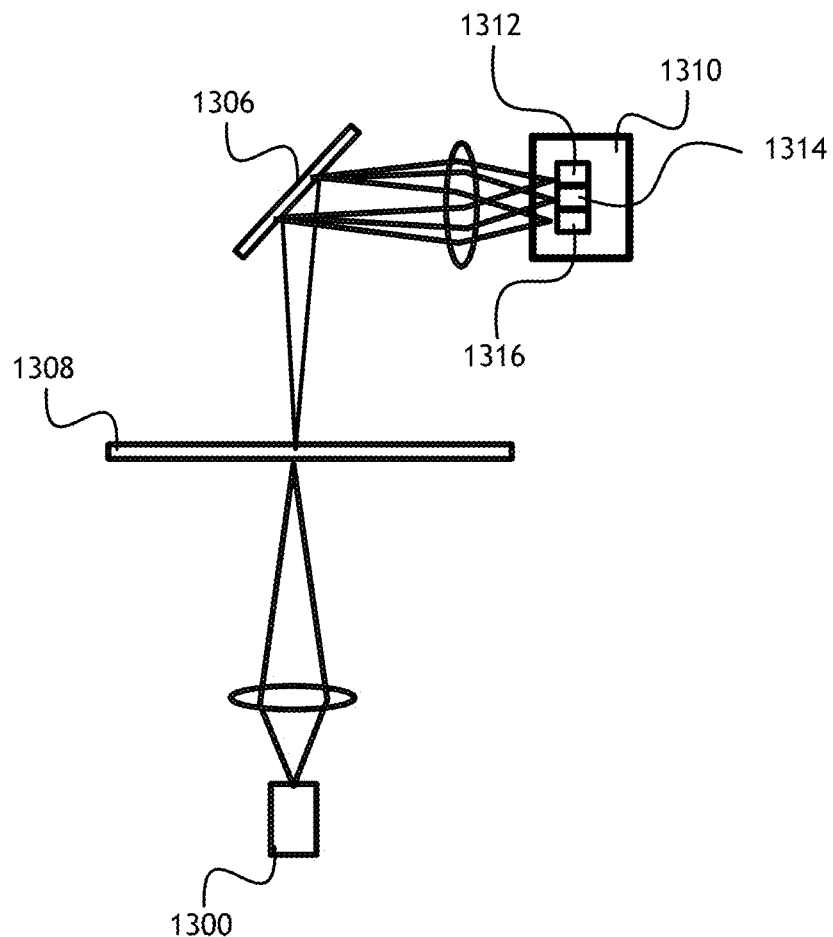
FIG. 13 shows a block diagram of a camera having more than one line sensor capturing images of a semiconductor wafer illuminated by an illuminator and separated by a diffraction grating.

Referring to FIG. 13, a block diagram of a camera having more than one line sensor capturing images of a semiconductor wafer illuminated by an illuminator and separated by a diffraction grating is shown. Such embodiment may include an illuminator 1300. The illuminator 1300 may illuminate a semiconductor wafer 1308 so as to transmit light through the semiconductor wafer 1308 to a line camera 1310. Light transmitted through the semiconductor wafer 1308 may reflect off of a diffraction grating 1306. Light reflecting off of a diffraction grating 1306 may be separated into different wavelength bands. Light reflecting off of the diffraction grating 1306 corresponding to each of the wavelength bands may be focused on a separate line sensor 1310, 1312, 1314 within the line camera 1310 such that each line sensor 1310, 1312, 1314 records light in a different wavelength band.

Figure 14:
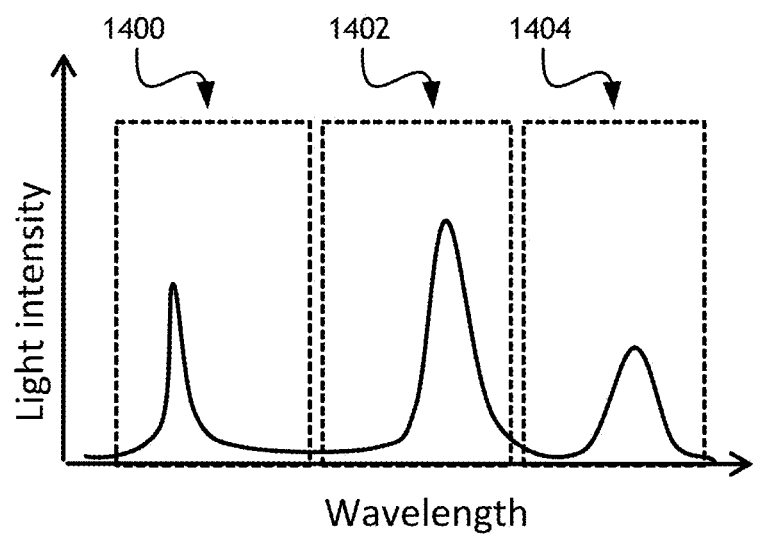
FIG. 14 shows a chart of light intensity over a range of wavelengths and the bands captured by one or more line sensors in a line camera.

Referring to FIG. 14, a chart of light intensity over a range of wavelengths and the bands captured by one or more line sensors in a line camera is shown. The chart shows an exemplary graph of light intensity compared to wavelength of either transmitted or reflected light depending on the embodiment. Systems such as those depicted in FIG. 12 and FIG. 13 may include a line camera having more than one line sensor. Each line sensor may capture a specific band of wavelengths. For example, a first line sensor may capture light in a first wavelength band 1400, a second line sensor may capture light in a second wavelength band 1402 and a third line sensor may capture light in a third wavelength band 1404. Reflected or transmitted light may be separated into wavelength bands by spectral filters, diffraction gratings or any other means known in the art.

The different wavelengths in the photoluminescence light emitted by a semiconductor wafer may contain different information about different types of defects inside the semiconductor wafer. Having separate images simultaneously acquired at different imaging wavelengths may be advantageous in classifying defects, and therefore more accurately measure wafer quality.

Figure 15:
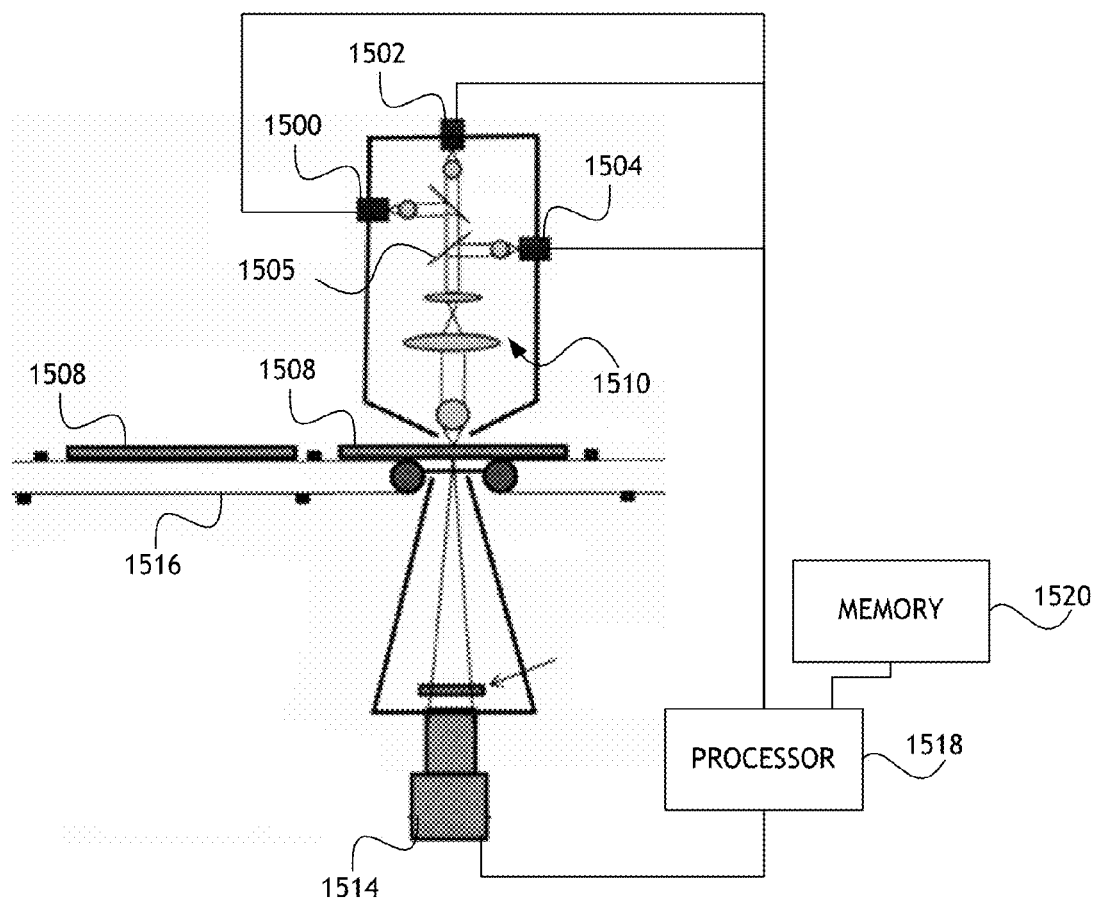
FIG. 15 shows a block diagram of a system for imaging a moving semiconductor wafer with three different illuminators.
Figure 16:
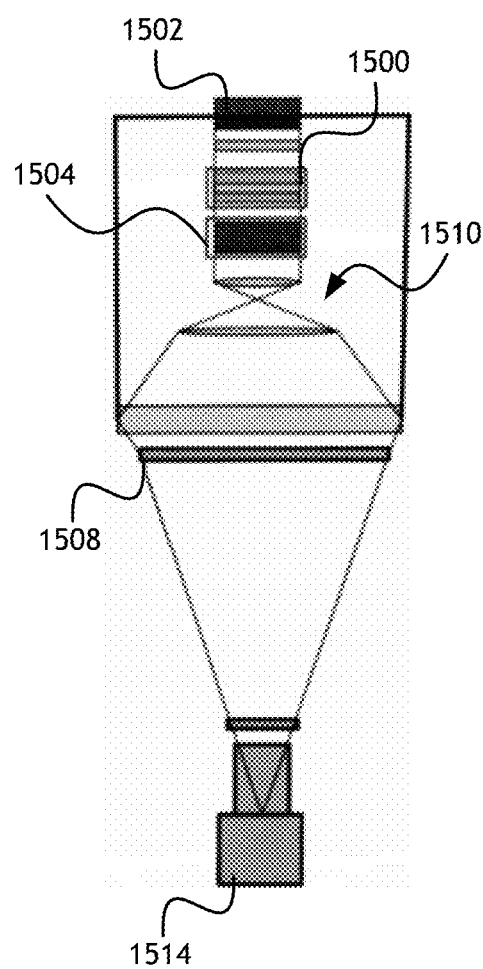
FIG. 16 shows a side view block diagram of the system in FIG. 8.

Referring to FIG. 15 and FIG. 16, a block diagram of a system for imaging a moving semiconductor wafer with three different illuminators is shown. The system may include a first in-line illuminator 1500 for projecting light onto a semiconductor wafer 1508. The first in-line illuminator 1500 may project light at some specific wavelength onto the surface of the semiconductor wafer 1508. The system may also include a second in-line illuminator 1502 for projecting light onto a semiconductor wafer 1508. The second in-line illuminator 1502 may project light at some specific wavelength onto the surface of the semiconductor wafer 1508 different from the wavelength of the first in-line illuminator 1500. The first in-line illuminator 1500 or second in-line illuminator 1502 may project light through splitters or other optical components 1510 such that each in-line illuminator 1500, 1502 may illuminate the same relative location of the semiconductor wafer 1508, at the same relative angle. The wavelengths of the first in-line illuminator 1500 and the second in-line illuminator 1502 may be, but are not limited to, red, near infrared and infrared.

The system may also include an imaging device 1514 to capture images of the semiconductor wafer 1508 produced by transmitted light from the first in-line illuminator 1500 or second in-line illuminator 1502.

The system may include a processor 1518 and a memory 1520 for controlling the in-line illuminators 1500, 1502 and imaging device 1514. The processor 1518 may be programmed to drive the first in-line illuminator 1500 and the second in-line illuminator 1502 to produce pulses of light at a certain frequency, offset from each other such that only one in-line illuminator 1500, 1502 illuminates the semiconductor wafer 1508 at a time. Furthermore, the processor 1518 may be programmed to synchronize the imaging device 1514 shutter to the frequencies of the in-line illuminators 1500, 1502 to capture separate images produced by each in-line illuminator 1500, 1502. In one embodiment, each in-line illuminator 1500, 1502 may illuminate a line in the same location so that the imaging device 1514 (a line camera) can capture a line image derived from each in-line illuminator 1500, 1502 sequentially. The processor 1518 may over or under sample the images depending on the number of lines captured within the optical point spread function to produce an interleaved line image. The processor 1518 may then separate the interleaved line image into separate two dimensional semiconductor wafer images for algorithmic processing and analysis.

The system may further include a third in-line illuminator 1504. The third in-line illuminator 1504 may project light at some specific wavelength onto the surface of the semiconductor wafer 1508 different from the wavelength of either the first in-line illuminator 1500 or the second in-line illuminator 1502. The third in-line illuminator 1504 may project light through splitters or other optical components such that each in-line illuminator 1500, 1502, 1504 may illuminate the same relative location of the semiconductor wafer 1508, at the same relative angle. The processor 1518 may be further programmed to drive the third in-line illuminator 1504 at a certain frequency corresponding to the frequencies of the first in-line illuminator 1500 and the second in-line illuminator 1502, and operate the imaging device 1514 shutter, such that the imaging device 1514 captures distinct images produced by each of the in-line illuminators 1500, 1502, 1504.

The system may also include a wafer moving device 1516 such as a belt to move semiconductor wafers 1508 through the illuminating and imaging apparatus.

Figure 17:
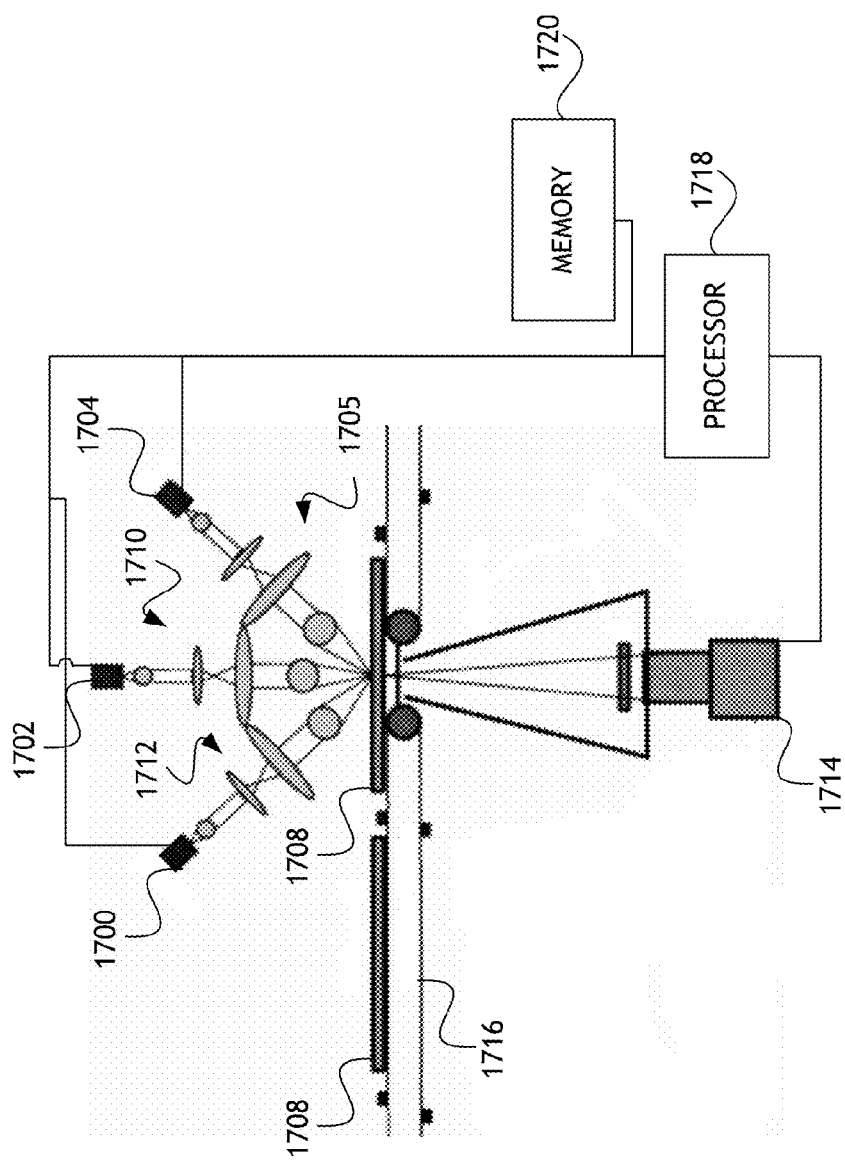
FIG. 17 shows a block diagram of a system for imaging a moving semiconductor wafer with three wavelength illuminators.

Referring to FIG. 17, a block diagram of a system for imaging a moving semiconductor wafer with three wavelength illuminators is shown. The system may include a first wavelength illuminator 1700 and lens assembly 1712 for projecting light onto a semiconductor wafer 1708. The first wavelength illuminator 1700 may project light at some specific wavelength onto the surface of the semiconductor wafer 1708. The system may also include a second wavelength illuminator 1702 and lens assembly 1710 for projecting light onto a semiconductor wafer 1708. The second wavelength illuminator 1702 may project light at some specific wavelength onto the surface of the semiconductor wafer 1708 different from the wavelength of the first wavelength illuminator 1700. The wavelengths of the first wavelength illuminator 1700 and the second wavelength illuminator 1702 may be, but are not limited to, red, near infrared and infrared.

The system may also include an imaging device 1714 to capture images of the semiconductor wafer 1708 produced by transmitted light from the first wavelength illuminator 1700 or second wavelength illuminator 1702.

The system may include a processor 1718 and a memory 1720 for controlling the wavelength illuminators 1700, 1702 and imaging device 1714. The processor 1718 may be programmed to drive the first wavelength illuminator 1700 and the second wavelength illuminator 1702 to produce pulses of light at a certain frequency, offset from each other such that only one wavelength illuminator 1700, 1702 illuminates the semiconductor wafer 1708 at a time. Furthermore, the processor 1718 may be programmed to synchronize the imaging device 1714 shutter to the frequencies of the wavelength illuminators 1700, 1702 to capture separate images produced by each wavelength illuminator 1700, 1702. In one embodiment, each wavelength illuminator 1700, 1702 may illuminate a line in the same location so that the imaging device 1714 (a line camera) can capture a line image derived from each wavelength illuminator 1700, 1702 sequentially. The processor 1718 may over or under sample the images depending on the number of lines captured within the optical point spread function to produce an interleaved line image. The processor 1718 may then separate the interleaved line image into separate two dimensional semiconductor wafer images for algorithmic processing and analysis.

The system may further include a third wavelength illuminator 1704 and lens assembly 1705. The third wavelength illuminator 1704 may project light at some specific wavelength onto the surface of the semiconductor wafer 1708 different from the wavelength of either the first wavelength illuminator 1700 or the second wavelength illuminator 1702. The processor 1718 may be further programmed to drive the third wavelength illuminator 1704 at a certain frequency corresponding to the frequencies of the first wavelength illuminator 1700 and the second wavelength illuminator 1702, and operate the imaging device 1714 shutter, such that the imaging device 1714 captures distinct images produced by each of the wavelength illuminators 1700, 1702, 1704.

The system may also include a wafer moving device 1716 such as a belt to move semiconductor wafers 1708 through the illuminating and imaging apparatus.

Figure 18:
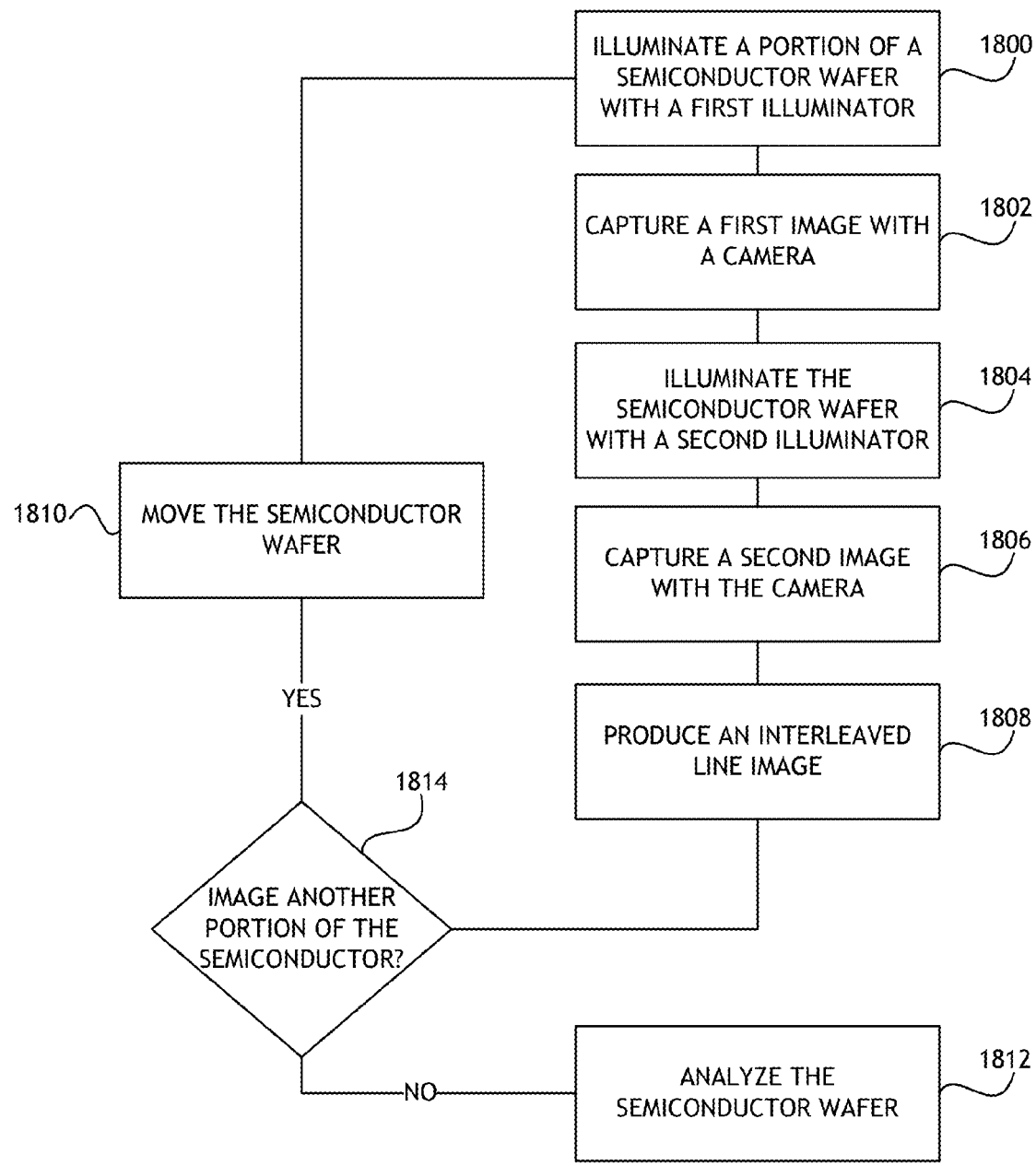
FIG. 18 shows a flowchart of a method for imaging a semiconductor wafer with one camera and a plurality of illuminators.

Referring to FIG. 18, a flowchart of a method for imaging a semiconductor wafer with one camera and a plurality of illuminators is shown. A processor may illuminate 1800 a portion of a moving semiconductor wafer with a first illuminator illuminating a line the width of the wafer and capture 1802 a first line image with a line imaging device. The processor may then illuminate 1804 the portion of the semiconductor with a second illuminator and capture 1806 a second line image with the same camera. The processor may produce 1808 an interleaved line image using the first and second image, storing the interleaved line image in memory. A processor may determine 1814 whether or not additional portions of the semiconductor wafer should be imaged. If additional portions of the semiconductor wafer should be imaged, the semiconductor wafer may move 1810, and the process may repeat. The next line image from the first illuminator is captured and then another line image from the second illuminator is captured. This cycle may repeat producing a stream of lines which consist of line images from the first illuminator and line images from the second illuminator interleaved along the length of the semiconductor wafer. The first illuminator and second illuminator may be illuminators operating at different wavelengths. Alternatively, the first illuminator and the second illuminator may be illuminators positioned to illuminate the semiconductor wafer at different angles. If the processor determines that no additional portions of the semiconductor wafer should be imaged, the processor may deconstruct the interleaved image into separate contiguous images each of one wavelength or angle for further analysis. The processor may then analyze 1812 the semiconductor wafer for defects or areas of interest. Three or four illuminators at different wavelengths and angles may also be interleaved in this fashion.

The images produced by the present invention may be useful to improve cell efficiency. The system may also combine multiple low angle infrared illuminators to generate tunneling optical effects which may enable direction independent micro-crack detection. The system may also measure surface roughness using a dark field mode.

The present invention utilizes fewer components than prior art systems, and may therefore be more cost effective and more reliable. A single camera can capture several independent images rather than using multiple cameras. A system utilizing the present invention may also be cheaper to construct and operate. The present invention allows for the use of line cameras as opposed to other cameras currently used in semiconductor inspection. Line cameras may be cheaper and provide superior resolution. Furthermore, the size of the system may be reduced.

It is believed that the present invention and many of its attendant advantages will be understood by the foregoing description, and it will be apparent that various changes may be made in the form, construction, and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A system for inspecting semiconductor wafers comprising:
   a camera configured to capture images of a semiconductor wafer; and
   a plurality of illuminators configured to illuminate the semiconductor wafer,
   wherein:
      each of the plurality of illuminators is configured to sequentially illuminate the semiconductor wafer in distinct wavelength band;
      the camera is configured to sequentially capture a plurality of images produced by each of the plurality of illuminators, each of the plurality of images in a distinct wavelength band; and
      the camera is further configured to interleave the sequentially captured images into a single image.

2. The system of claim 1, further comprising a conveyor configured to move the semiconductor wafer between the plurality of illuminators and the camera, wherein the camera is further configured to capture images of the semiconductor wafer produced by each of the plurality of illuminators line-by-line.

3. The system of claim 1, wherein:
   each of the plurality of illuminators is further configured to produce a pulse; and
   the camera further comprises a shutter configured to operate synchronously with the pulses produced by each of the plurality of illuminators.

4. The system of claim 1, wherein at least one of the illuminators comprises a laser bar.

5. The system of claim 1, wherein the camera comprises a plurality of wavelength band filters configured to switch line-by-line synchronously with a camera line rate.

6. The system of claim 1, wherein:
   a first illuminator in the plurality of illuminators is configured to illuminate the semiconductor wafer at a first angle; and
   a second illuminator in the plurality of illuminators is configured to illuminate the semiconductor wafer at a second angle.

7. The system of claim 1, further comprising a plurality of angled illuminators configured to illuminate the semiconductor wafer at different azimuth angles, wherein:
   a first angled illuminator in the plurality of angled illuminators is configured to illuminate the semiconductor wafer at a first angle; and
   a second angled illuminator in the plurality of angled illuminators is configured to illuminate the semiconductor wafer at a second angle.

8. The system of claim 7, further comprising a plurality of cameras, at least two of the plurality of cameras configured to capture images in distinct wavelength bands.

9. The system of claim 1, wherein the camera comprises two or more line sensors, each of the two or more line sensors configured to capture a separate line image of a semiconductor wafer.

10. The system of claim 9, further comprising two or more spectral filters, each of the two or more spectral filters associated with one of the two or more line sensors.

11. A system for inspecting semiconductor wafers comprising:
    a camera configured to capture images of a semiconductor wafer; and
    a plurality of illuminators configured to illuminate the semiconductor wafer,
    wherein:
       each of the plurality of illuminators is configured to sequentially illuminate the semiconductor wafer at a particular angle;
       the camera is configured to sequentially capture a plurality of images produced by each of the plurality of illuminators; and
       the camera is further configured to interleave the sequentially captured images into a single image.

12. The system of claim 11, further comprising a conveyor configured to move the semiconductor wafer between the plurality of illuminators and the camera, wherein the camera is further configured to capture images of the semiconductor wafer produced by each of the plurality of illuminators line-by-line.

13. The system of claim 11, wherein:
    each of the plurality of illuminators is further configured to produce a pulse; and
    the camera further comprises a shutter configured to operate synchronously with the pulses produced by each of the plurality of illuminators.

14. The system of claim 11, wherein at least one of the illuminators comprises a laser bar.

15. The system of claim 11, wherein:
    a first illuminator in the plurality of illuminators is configured to illuminate the semiconductor wafer in a first wavelength band; and
    a second illuminator in the plurality of illuminators is configured to illuminate the semiconductor wafer in a second wavelength band.

16. The system of claim 11, wherein the camera comprises two or more line sensors, each of the two or more line sensors configured to capture a separate line image of a semiconductor wafer.

17. The system of claim 16, further comprising two or more spectral filters, each of the two or more spectral filters associated with one of the two or more line sensors.

18. A system for inspecting semiconductor wafers comprising:
    a plurality of cameras, each of the plurality of cameras comprising a wavelength band filter; and
    a plurality of illuminators configured to illuminate the semiconductor wafer,
    wherein:
       each of the plurality of illuminators is configured to sequentially illuminate the semiconductor wafer in a particular wavelength band;
       each of the plurality of cameras is configured to sequentially capture a plurality of images of the semiconductor wafer in a particular wavelength band; and
       the plurality of cameras is further configured to interleave the plurality of images into a single image.

19. The method of claim 18, wherein the camera comprises two or more line sensors, each of the two or more line sensors configured to capture a separate line image of a semiconductor wafer.

20. A method for inspecting a semiconductor wafer comprising:
    illuminating the semiconductor wafer with a first illuminator;
    capturing a first image of the semiconductor wafer with a camera;
    illuminating the semiconductor wafer with a second illuminator;
    capturing a second image of the semiconductor wafer with the camera; and
    interleaving the first image and second image,
    wherein:
        the first illuminator is configured to illuminate the semiconductor wafer in a first wavelength band; and
        the second illuminator is configured to illuminate the semiconductor wafer in a wavelength band range.

21. The method of claim 20, wherein:
    the first illuminator is configured to illuminate the semiconductor wafer at a first angle; and
    the second illuminator is configured to illuminate the semiconductor wafer at a second angle.

22. The method of claim 20, further comprising moving the semiconductor wafer from a first position interposed between the camera and the first and second illuminators to a second position interposed between the camera and the first and second illuminators.

23. The method of claim 20, further comprising detecting at least one of wafer and cell micro-cracks in the semiconductor wafer.

24. A method for inspecting a semiconductor wafer comprising:
    illuminating the semiconductor wafer with a first illuminator;
    capturing a first image of the semiconductor wafer with a camera;
    illuminating the semiconductor wafer with a second illuminator;
    capturing a second image of the semiconductor wafer with the camera; and
    interleaving the first image and second image,
    wherein:
        the first illuminator is configured to illuminate the semiconductor wafer at a first angle; and
        the second illuminator is configured to illuminate the semiconductor wafer at a second angle.

25. The system of claim 24, wherein:
    the first illuminator is configured to illuminate the semiconductor wafer in a first frequency range; and
    the second illuminator is configured to illuminate the semiconductor wafer in a second frequency range.

26. The system of claim 24, further comprising moving the semiconductor wafer from a first position interposed between the camera and the first and second illuminators to a second position interposed between the camera and the first and second illuminators.

27. The method of claim 24, further comprising detecting at least one of wafer and cell micro-cracks in the semiconductor wafer.

28. The method of claim 24, wherein the camera comprises two or more line sensors, each of the two or more line sensors configured to capture a separate line image of a semiconductor wafer.

* * * * *